United States Patent [19]

Mann

[11] Patent Number: 5,273,754

[45] Date of Patent: Dec. 28, 1993

[54] APPETITE SUPPRESSANT COMPOSITION AND METHOD RELATING THERETO

[76] Inventor: Morris A. Mann, 3310 W. Bell Rd., Suite 1001, Phoenix, Ariz. 85023

[21] Appl. No.: 857,571

[22] Filed: Mar. 27, 1992

[51] Int. Cl.$^5$ .............................................. A61K 9/68
[52] U.S. Cl. ................................ 424/440; 424/195.1; 424/58; 424/441; 424/151; 424/465
[58] Field of Search ................ 424/195.1, 76.1, 441, 424/451, 58, 465, 440; 426/597; 514/627

[56] References Cited

U.S. PATENT DOCUMENTS

| | | | |
|---|---|---|---|
| 3,408,200 | 10/1968 | Teichman et al. | 99/2 |
| 4,197,319 | 4/1980 | Betz et al. | 426/2 |
| 4,423,030 | 12/1983 | Hayes | 424/58 |
| 4,680,313 | 7/1987 | Iwai | 514/627 |
| 4,833,128 | 5/1989 | Solomon et al. | 514/23 |
| 4,843,071 | 6/1989 | Hohenwarter | 424/465 |
| 4,946,701 | 8/1990 | Tsai | 426/597 |

FOREIGN PATENT DOCUMENTS 60-262571 12/1985 Japan .
63-188349 8/1988 Japan .

OTHER PUBLICATIONS

Ritter and Ladenheim, *Am. J. Physiol.* 248 (4 Pt 2):R501–R504, 1985.
Yox et al., *Am. J. Physiol.* 260 (4 Pt 2):R681–R687, 1991.
Yox and Ritter, *Am. J. Physiol.* 255 (4 Pt 2):R569–R574, 1988.
South and Ritter, *Peptides* 9(3):601–612, 1988.
Castonguay and Bellinger, *Physiol. Behav.* 40(3):337–342, 1987.
MacLean, *Regul. Pept.* 11(4):321–333, 1985.
Butler et al., *Am. J. Clin. Nutrit.* 34:2045–2047, 1981.
*Chem. Abstr.* 127574q (1988).

*Primary Examiner*—Thurman K. Page
*Assistant Examiner*—William E. Benston, Jr.
*Attorney, Agent, or Firm*—Seed and Berry

[57] ABSTRACT

There is disclosed an appetite suppressant composition for oral administration. The composition includes a heating and a cooling carminative substance, and may also include an amino acid and an anxiolytic substance. Also disclosed are methods for decreasing appetite by oral administration of the appetite suppressant composition, and for manufacture of the appetite suppressant composition.

22 Claims, No Drawings

APPETITE SUPPRESSANT COMPOSITION AND METHOD RELATING THERETO

TECHNICAL FIELD

This invention relates generally to an appetite suppressant and methods related thereto, and more specifically to a composition which decreases appetite thereby reducing food and caloric intake and leading to a decrease in weight.

BACKGROUND OF THE INVENTION

Obesity caused by excessively high caloric intake and accumulation of surplus fat often leads to various types of degenerative diseases. Dieting, bariatrics and cytotherapy is of major concern to patients who suffer from obesity-caused diseases and also to healthy people who, for cosmetic reasons, wish to control their caloric intake and thereby decrease their weight.

Dieting often requires that significant limitations be placed on the amount of caloric intake, and the amount of fat and carbohydrates consumed by an individual are invariably diminished in a successful dietary plan. However, due to the inherent causes of obesity and overeating, dieting by itself is often unsuccessful in achieving the patient's goals. There are two primary reasons for this. First, there is an immense amount of patience required by the dieter to lose significant amounts of weight. Second, and perhaps more important, are the inherent reasons that people eat to excess. For example, it is well known that the vast majority of over-eating is done to satisfy anxiety. Thus, caloric intake often is not engaged in for the purpose of satisfying hunger and meeting metabolic needs, but to satisfy secondary needs in the individual's life.

In the past, appetite suppression has been accomplished by the use of centrally-acting neuro-stimulants such as cocaine, methamphetamine hydrochloride, dextroamphetamine sulfate and other derivatives of the amphetamine molecule. These drugs typically are extremely effective for a short period of time, but tachyphylaxis invariably develops and there are inherent side-effects with the use of such drugs. Other approaches have also been tried without a great deal of success, including a high fiber intake with unmetabolizable foods (such as konjak, also known as glucomannin) and physical methods (such as exercise). Other approaches that have been used include the use of local anesthetics. However, these compounds have proved unsuccessful because they are easily hydrolyzed in the stomach by hydrochloric acid which is secreted by the chief cells in the stomach lining. Injectable cholecystokinin has also been considered as a methodology for decreasing the sensation of appetite, but this method requires intravenous injection on a regular basis.

Accordingly, there is a need in the art for an appetite suppressant which will suppress appetite by exerting a local gastric effect, as well as central effects such as a perceived nutrient overload effect, thereby diminishing appetite for a significant period of time. There is also a need for an appetite suppressant which avoids the development of tachyphylaxis. This invention fulfills these needs, and provides other related advantages.

SUMMARY OF THE INVENTION

Briefly stated, in one embodiment, the present invention discloses an oral appetite suppressant composition which includes both a heating and cooling carminative substance. Heating carminative substances include capsaicin, an amine present in plants such as capsicum (i.e., cayenne pepper) and paprika, as well as cinnamon, mustard, ginger, pepper, clove, mace, papaya seed, and mixtures thereof. Cooling carminative substances include peppermint, menthol, spearmint, carvone, and mixtures thereof. In addition to the heating and cooling carminative substances, the oral appetite suppressant composition may also include an amino acid and/or an anxiolytic substance. The amino acid may be L-methionine, D-phenylalanine, glycine and mixtures thereof. The anxiolytic substances include: valerian, damiana, chamomile, kava kava, passionflower, hops, skullcap, St. John's Wort, and mixtures thereof.

In another embodiment, the present invention discloses a method for decreasing appetite by oral administration of an effective amount of the appetite suppressant composition. In yet a further embodiment, a method for manufacturing an oral appetite suppressant is disclosed.

DETAILED DESCRIPTION OF THE INVENTION

The appetite suppressant composition of the present invention includes both a heating carminative substance and a cooling carminative substance. Carminative substances are known agents which induce expulsion of gas from the stomach and intestines. As used herein, the term "heating carminative substance" is a substance having a gastric heating effect and which exhibits a local anesthetic effect in the stomach (particularly upon the gastric nerves controlling hunger) when administered orally at a sufficient dose.

Capsaicin is a preferred heating carminative substance, and is represented by the following chemical structure:

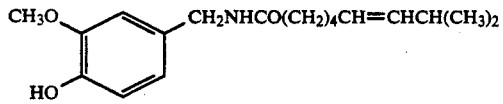

An advantage of capsaicin over other local anesthetics (such as procaine hydrochloride) is that it is not subject to rapid hydrolyzation in the stomach. While standardized oleoresin capsicum (which contains capsaicin) is preferred, crystalline capsaicin may also be used.

Capsaicin may generally be characterized as a vanillylamide having the structure:

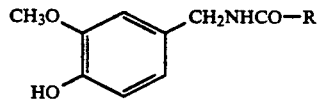

wherein R is a saturated or unsaturated, branched or unbranched, alkyl moiety having 1–20 carbon atoms (preferably 9–11 carbon atoms) and optionally substituted with one or more hydroxy moieties. While capsaicin is a preferred heating carminative substance, vanillylamides of the above structure may also be utilized. Such vanillylamides are known compounds and may readily be synthesized by standard organic synthesis techniques. For example, vanillylamides suitable for use in the present invention (and the syntheses thereof) are disclosed in U.S. Pat. No.4,680,313 (which is incorporated herein by reference).

Additional heating carminative substances of the present invention include capsicum or "cayenne pepper" (known commercially as "African Chillies"—*Capsicum frutescens* L., Solanaceae; "Tabasco pepper"'—*Capsicum annuum* L., var. conoides Irish; "Louisiana Long Pepper"—*Capsicum annuum* var. longum Sendt; "Louisiana Sport Pepper"—hybrid between the Honka variety of Japanese Capsicum and the Old Louisiana Sport Capsicum, Fam. Solanaceae), and paprika (*Capsicum annuum* var. largum). Both capsicum and paprika contain capsaicin. Non-capsaicin containing heating carminative substances include: cinnamon (*Cinnamomum loureirii*); mustard (*Brassica nigra, B. juncea, Sinapis alba*); ginger (*Zingibar officinalis*); pepper (*Piper nigrum*); clove (*Syzygium aromaticum*); mace (*Myrestica fragrans*); papaya seed (*Carica papaya*); and mixtures thereof.

The heating carminative substance is present in the appetite suppressant composition in an amount which, when administered orally, is effective in diminishing appetite. Preferably, the heating carminative substance is present in a suitable oral form in an amount ranging from 1 mg to 1000 mg, and more preferably from 5 mg to 500 mg, and most preferably from 10 mg to 250 mg (based on an activity of 250,000 Scoville units), and is typically administered one to six times (preferably two to three times) during each 24-hour period.

As used herein, a "cooling carminative substance" is present in the appetite suppressant composition to diminish any undesirable burning sensation that sometimes results upon the ingestion of the heating carminative substance (such as crystalline capsaicin or oleoresin capsicum). Preferred cooling carminative substances include peppermint (*Mentha piperita*), menthol (peppermint camphor), spearmint (*Mentha spicata, Mentha viridis*), carvone, and mixtures thereof. Preferably, the cooling carminative substance is menthol (which also possesses a topical anesthetic effect).

The cooling carminative substance is present in the appetite suppressant composition in an amount which, when administered orally, is effective in diminishing the burning sensation. Preferably, the cooling carminative substance is present in a suitable oral form in an amount ranging from 1 mg to 1000 mg, typically from 1 mg to 500 mg, preferably from 2 mg to 250 mg, and most preferably from 5 mg to 100 mg.

In addition to the heating and cooling carminative substances, the appetite suppressant composition may further include an amino acid selected from L-methionine, D-phenylalanine, glycine, and mixtures thereof. Preferably, the amino acid is L-methionine, a primary amine, and formed in high concentration in legumes. L-methionine is believed to selectively effect the appetite control in the septal region of the hippocampus, resulting in a perception by the brain of significant food intake, and thereby producing a sensation of satiety. D-pbenylalanine is known to increase endorphin levels in the body and, since endorphins are released after a large meal, it is believed to contribute to a feeling of satiety. Glycine stimulates the release of glucagon, which raises blood glucose levels that have fallen too low. This aids in the prevention of overeating by those with hypoglycemia (low blood sugar). Thus, the presence of one or more of these amino acids in the composition imparts further advantages relating to appetite suppression. Preferably, the amino acid is present in the appetite suppressant composition in an amount ranging from 5 mg to 2000 mg.

The appetite suppressant composition may also include an anxiolytic substance which serves to reduce anxiety and its attendant overeating. Such substances include: valerian (*Valeriana officinalis* L., Valerianaceae habit), damiana (*Turnera diffusa*), chamomile (*Matricaria chamomilla, Chamaemelum nobile*), kava kava (*Piper methysticum*), passionflower (*Passiflora incarnata*), hops (*Humulus lupulus*), skullcap (*Scutellaria lateriflora*), St. John's Wort (*Hypericum perforatum*), and mixtures thereof. Preferably, the anxiolytic substance is valerian, damiana, chamomile, or a mixture thereof, and is present in the appetite suppressant composition in an amount ranging from 10 mg to 1000 mg.

The ingredients of the appetite suppressant composition may be used without any special treatment, or extracts thereof may be utilized. For example, the capsicum herb may be powdered and incorporated into capsule form. Alternatively, the capsicum herb may be extracted with, for example, an alcohol/water mixture, and the extractant dried by spray drying or evaporation.

The appetite suppressant composition of the present invention is manufactured by combining all ingredients in a form suitable for oral administration, and preferably as a capsule or tablet. For example, the appetite suppressant composition of the present invention may be encapsulated (such as in a coating of hard gelatin) for oral administration. Such techniques are well known in the art (see, e.g., Baker, Richard, *Controlled Release of Biologically Active Agents*, John Wiley & Sons, 1986). Inert fillers may also be present in oral (e.g., capsule or tablet) form.

When formulated as capsules, the appetite suppressant composition is preferably administered one to three times a day, and preferably 45 minutes to an hour prior to any given meal. Administration of the appetite suppressant composition in oral form decreases appetite and exhibits a cumulative effect. Such administration results in appetite suppression for a considerable period of time, including up to 12 hours into the following day. The amount of appetite suppressant composition administered is sufficient to suppress appetite. While the oral dosage may contain from 2 mg to 5000 mg (i.e., total weight of all active ingredients), a single capsule or tablet containing over 1000 mg may be too large to easily swallow. Thus, the composition may be administered in multiple capsule or tablet form. In addition, the total weight of all active ingredients will depend on the form of ingredients used. For example, less crystalline capsaicin may be used compared to powered capsicum herb and yet achieve the same level of appetite suppression. One skilled in the art could readily determine the precise quantity of ingredients depending upon the form of ingredients.

The following examples are provided for purposes of illustration and are not intended to be limiting.

EXAMPLES

EXAMPLE 1

A capsule formulation was made by powdering the following ingredients and then encapsulating:

| | |
|---|---|
| Capsicum powdered herb | 200 mg. |
| Valerian powdered herb | 250 mg. |
| Damiana powdered herb | 250 mg. |
| Menthol | 100 mg. |

| | | |
|---|---|---|
| | 800 mg. | Total/Capsule |

A single capsule was taken orally by two different persons at approximately 2 p.m. Their appetites did not greatly diminish during the first six hours (i.e., until 8 p.m.). However, both persons reported that they did not feel hungry towards the end of the day (approximately 11:00 p.m.), nor did they have any appreciable appetite until approximately noon the following day.

EXAMPLE 2

The following capsule formula was prepared using concentrated herbal extracts. All ingredients were powdered and then encapsulated (#2 gelatin capsules, Capsugel, Greenwood, S.C.):

| | | |
|---|---|---|
| Capsicum extract | 60 mg. | |
| L-Methionine | 60 mg. | |
| Valerian extract | 30 mg. | |
| Damiana extract | 30 mg. | |
| Menthol | 60 mg. | |
| | 300 mg. | Total/Capsule |

Fifteen patients on the Medifast ® weight loss plan were administered the above capsule formulation twice a day (1 hour prior to lunch and supper) for 42 days. The Medifast ® weight loss plan is a physician-supervised program of modified fasting used in the treatment of severe obesity. Typically, these patients have unsuccessfully tried many other weight loss programs prior to beginning at the Medifast ® clinic, and therefore represent an extremely difficult group in which to effect weight loss. At the end of the 42 days, the fifteen patients lost an average of 12 to 15 pounds. Patients on the same weight loss plan, but not taking the appetite suppressant, lost only an average of 9 pounds during the same time span. This difference is very significant and is believed to be the result of less "cheating" (i.e., eating foods not allowed on the Medifast ® program) on the part of the patients.

From the foregoing description, it will be apparent to one of ordinary skill in the art that certain modifications and changes can be made without departing from the spirit and scope of the invention.

I claim:

1. An oral appetite suppressant composition comprising a heating carminative substance and a cooling carminative substance, wherein the heating carminative substance is a vanillylamide, wherein the cooling carminative substance is selected from the group consisting of peppermint, menthol, spearmint, carvone, extracts thereof and mixtures thereof, and wherein the heating carminative substance is present in the composition in an amount which, when administered orally, is effective in diminishing appetite.

2. The composition of claim 1 wherein the vanillylamide is capsaicin.

3. An oral appetite suppressant composition comprising a heating carminative substance and a cooling carminative substance, wherein the heating carminative substance is selected from the group consisting of capsicum, paprika, cinnamon, mustard, ginger, pepper, clove, mace, papaya seed, extracts thereof, and mixtures thereof, wherein the cooling carminative substance is selected from the group consisting of peppermint, menthol, spearmint, carvone, extracts thereof and mixtures thereof, and wherein the heating carminative substance is present in the composition in an amount which, when administered orally, is effective in diminishing appetite.

4. The composition of claim 3 wherein the heating carminative substance is capsicum or an extract thereof.

5. The composition of claim 1 or 3 wherein the cooling carminative substance is menthol.

6. The composition of claim 1 or 3 wherein the heating carminative substance and cooling carminative substance are each present in an amount ranging from 1 mg to 1000 mg.

7. The composition of claim 1 or 3, further including an anxiolytic substance.

8. The composition of claim 9 wherein the anxiolytic substance is selected from the group consisting of valerian, damiana, chamomile, kava kava, passionflower, hops, skullcap, St. John's Wort, extracts thereof, and mixtures thereof.

9. The composition of claim 8 wherein the anxiolytic substance is valerian, damiana, chamomile, extracts thereof, or mixtures thereof.

10. The composition of claim 7 wherein the anxiolytic substance is present in an amount ranging from 10 mg to 1000 mg.

11. The composition of claim 1 or 3, further including an amino acid.

12. The composition of claim 11 wherein the amino acid is selected from the group consisting of L-methionine, D-phenylalanine, glycine, and mixtures thereof.

13. The composition of claim 12 wherein the amino acid is L-methionine.

14. The composition of claim 11 wherein the amino acid is present in an amount ranging from 5 mg to 2000 mg.

15. A method for decreasing appetite by exerting a local anesthetic effect in the stomach, comprising oral administration of an appetite suppressant composition, wherein said composition comprises a heating carminative substance and a cooling carminative substance, wherein the heating carminative substance is a vanillylamide, wherein the cooling carminative substance is selected from the group consisting of peppermint, menthol, spearmint, carvone, extracts thereof and mixtures thereof, and wherein the heating carminative substance is present in the composition in an amount which, when administered orally, is effective in diminishing appetite.

16. The method of claim 15 wherein the composition further includes an anxiolytic substance.

17. The method of claim 15 wherein the composition further includes an amino acid.

18. The method of claim 15 wherein the composition is administered in an amount ranging from 2 to 5000 mg.

19. A method for decreasing appetite by exerting a local anesthetic effect in the stomach, comprising oral administration of an appetite suppressant composition, wherein said composition comprises a heating carminative substance and a cooling carminative substance, wherein the heating carminative substance is selected from the group consisting of capsicum, paprika, cinnamon, mustard, ginger, pepper, clove, mace, papaya seed, extracts thereof, and mixtures thereof, wherein the cooling carminative substance is selected from the group consisting of peppermint, menthol, spearmint, carvone, extracts thereof and mixtures thereof, and wherein the heating carminative substance is present in the composition in an amount which, when administered orally, is effective in diminishing appetite.

20. The method of claim 19 wherein the composition further includes an anxiolytic substance.

21. The method of claim 19 wherein the composition further includes an amino acid.

22. The method of claim 19 wherein the composition is administered in an amount ranging from 2 to 5000 mg.

* * * * *

UNITED STATES PATENT AND TRADEMARK OFFICE
CERTIFICATE OF CORRECTION

PATENT NO. : 5,273,754
DATED : December 28, 1993
INVENTOR(S) : Morris A. Mann

It is certified that error appears in the above-indentified patent and that said Letters Patent is hereby corrected as shown below:

In Column 6, claim 8, line 12, delete "9" and substitute therefor —7—.

Signed and Sealed this

Twelfth Day of July, 1994

Attest:

BRUCE LEHMAN

*Attesting Officer*     *Commissioner of Patents and Trademarks*